(12) United States Patent
Dlubala

(10) Patent No.: US 8,288,547 B2
(45) Date of Patent: Oct. 16, 2012

(54) N-METHYLNALTREXONE ZWITTERION

(75) Inventor: Alain Dlubala, Les Angles (FR)

(73) Assignee: Sanofi, Paris (FR)

( * ) Notice: Subject to any disclaimer, the term of this patent is extended or adjusted under 35 U.S.C. 154(b) by 60 days.

(21) Appl. No.: 12/625,649

(22) Filed: Nov. 25, 2009

(65) Prior Publication Data

US 2010/0145051 A1 Jun. 10, 2010

Related U.S. Application Data

(60) Division of application No. 12/049,607, filed on Mar. 17, 2008, now Pat. No. 7,645,880, which is a continuation of application No. PCT/FR2007/001516, filed on Sep. 19, 2007.

(30) Foreign Application Priority Data

Sep. 21, 2006 (FR) ...................................... 06 08286

(51) Int. Cl.
*C07D 489/02* (2006.01)
(52) U.S. Cl. ......................................................... 546/45
(58) Field of Classification Search ....................... 546/45
See application file for complete search history.

(56) References Cited

U.S. PATENT DOCUMENTS 4,176,186 A 11/1979 Goldberg et al.

FOREIGN PATENT DOCUMENTS

WO WO 2004/043964 5/2004
WO WO 2006/127898 11/2006

OTHER PUBLICATIONS

Krassnig, R., et. al., A New and Efficient Synthesis of the µ Opioid Receptor antagonists 14-O-Methyl-and 14-O-Ethylnaloxone and -naltrexone, Heterocycles, vol. 47, No. 2. (1998), pp. 1029-1032.

*Primary Examiner* — Taofiq A Solola
(74) *Attorney, Agent, or Firm* — Serena Farquharson-Torres; Scully, Scott, Murphy & Presser, P.C.

(57) ABSTRACT

The invention discloses and claims N-Methylnaltrexone zwitterion, of formula (I), substantially in the anhydrous form or a hydrate thereof:

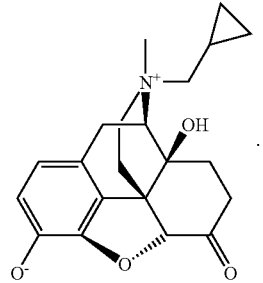

(I)

10 Claims, 1 Drawing Sheet

N-METHYLNALTREXONE ZWITTERION

CROSS REFERENCE TO RELATED APPLICATIONS

This application is a divisional of U.S. application Ser. No. 12/049,607, filed Mar. 17, 2008, now U.S. Pat. No. 7,645,880 which is a continuation of International application No. PCT/FR2007/001,516, filed Sep. 19, 2007, which is incorporated herein by reference in its entirety; which claims the benefit of priority of French Patent Application No. 06/08,286, filed Sep. 21, 2006.

BACKGROUND OF THE INVENTION

1. Field of the Invention

The present invention relates to N-Methylnaltrexone zwitterion substantially in the anhydrous form or a hydrate thereof.

2. Description of the Art

N-Alkyl quaternary derivatives of naltrexone (a nomenclature of naltrexone being (5α)-17-(cyclopropylmethyl)-4,5-epoxy-3,14-dihydroxymorphinan-6-one or N-cyclo-propyl-methylnoroxymorphone) are known for their therapeutic applications, especially N-methylnaltrexone, the use of which makes it possible to combine a morphine treatment in a patient, significantly reducing the adverse side effects of morphine and derivatives thereof, especially on the gastrointestinal tract.

The term "N-methylnaltrexone" more particularly means (R)—N-methylnaltrexone, i.e. the compound of (R) configuration relative to the nitrogen atom, it being well known to those skilled in the art that the (S)—N-methyl compound has activity opposite to that desired for accompanying a morphine-based treated.

The configuration of the quaternary ammonium of the N-methylnaltrexone having the formula below was determined by $^1$H NMR of the isolated (R) and (S) diastereoisomers:

(S) configuration of the ammonium (equatorial methyl): $R_1$ represents a methyl group and $R_2$ represents a methylcyclopropyl group, and (R) configuration of the ammonium (axial methyl): $R_2$ represents a methyl group and $R_1$ represents a methylcyclopropyl group.

The chemical shifts in $^1$H NMR of the methyl group (reference TMS or tetramethylsilane) are at 3.62 ppm for the (R) configuration and at 3.13 ppm for the (S) configuration.

U.S. Pat. No. 4,176,186 (Boehringer Ingelheim GmbH) describes quaternary noroxymorphone derivatives and also processes for preparing them. However, the described processes comprise conditions, especially of super atmospheric pressure, of necessary amount of reagent, and of conversion by column anion exchange, which are incompatible with the desired industrial application.

International Patent application, WO 2004/043 964 A2 describes a process at lower pressures, comprising the use of an anhydrous solvent system, especially 1-methyl-2-pyrrolidone, but which nevertheless still has drawbacks in terms of impurities, the imperative sufficiently low content of which inevitably leads to an unsatisfactory yield.

There was thus ever-increasing interest in having available a process for the industrial-scale production of such derivatives, under the best conditions in terms of production (safety and environment) and yield.

SUMMARY OF THE INVENTION

A process has now been found, entirely surprisingly and unexpectedly, for very advantageously improving both the implementation conditions in terms of safety, not only for the personnel but also for the environment, and the yield for the desired final product, i.e. an N-alkylnaltrexone halide, in particular N-methylnaltrexone bromide.

In accordance with the invention, a process comprising the steps according to Scheme 1 below may be performed.

Scheme 1:

N-Methylnaltrexone Bromide, starting from Noroxymorphone Hydrochloride

Noroxymorphone Hydrochloride
N-ALKYLATION

Br—CH₂—cyclopropyl / NaHCO₃ / Dimethylacetamide

Naitrexone
O-BENZYLATION

Benzyl bromide / K₃CO₃ / Acetone

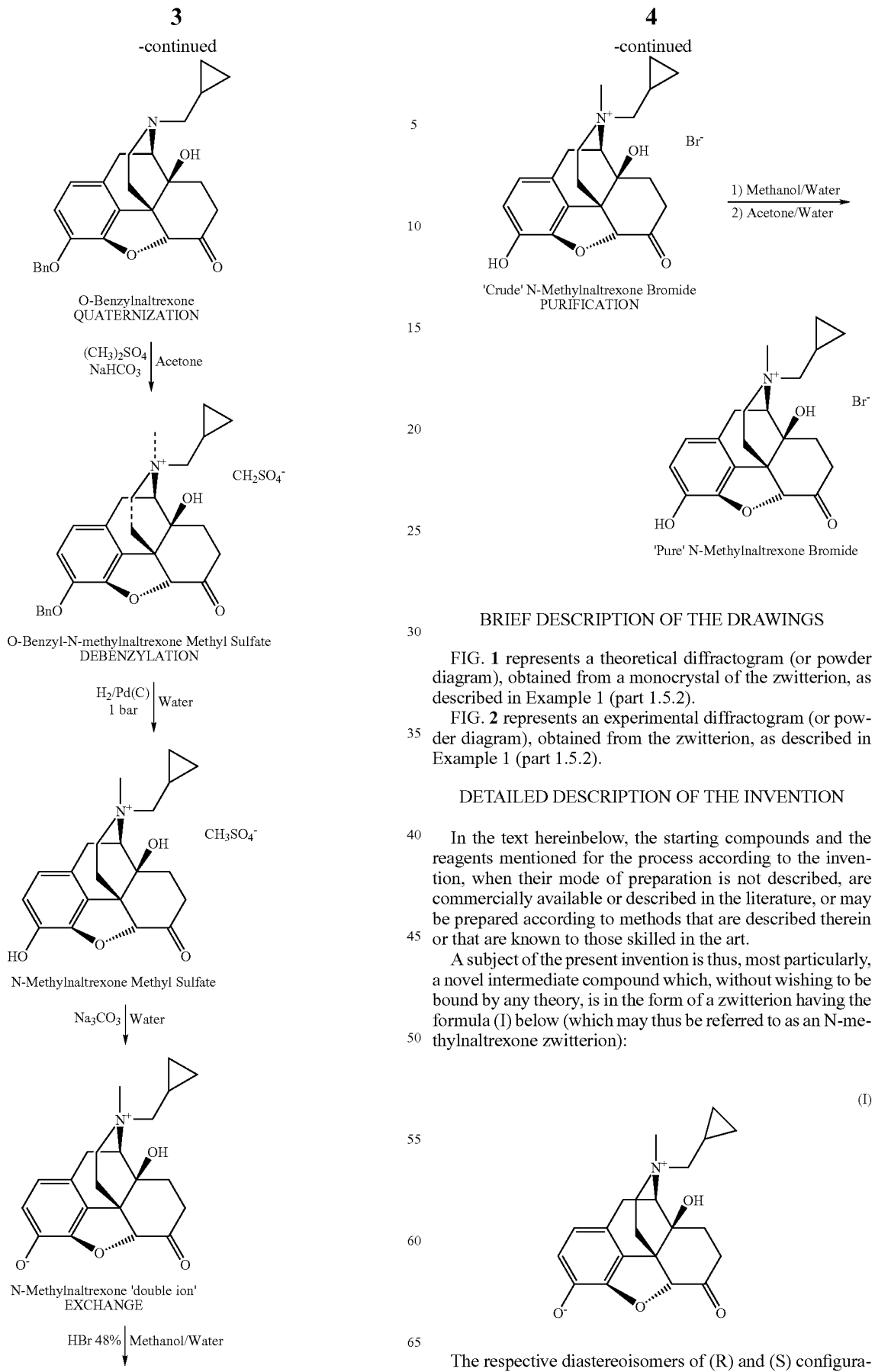

DETAILED DESCRIPTION OF THE INVENTION

Figure 1:
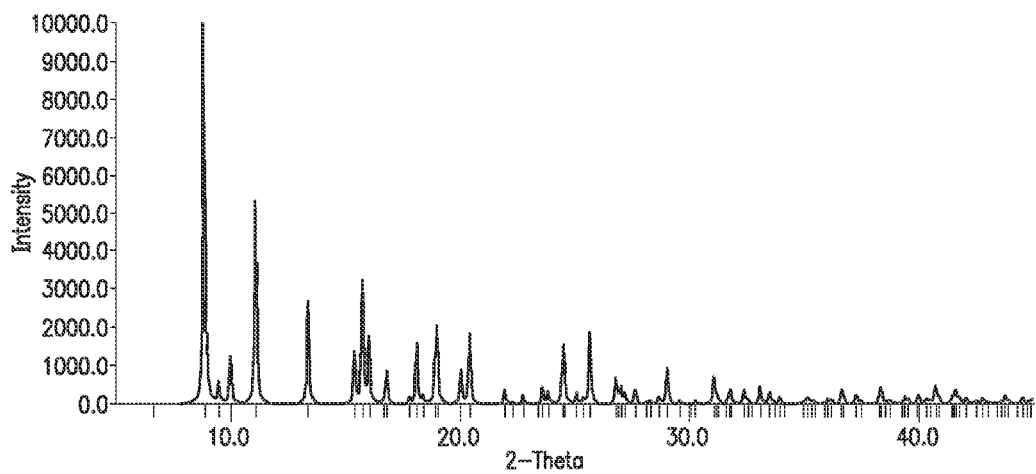
FIG. 1 represents a theoretical diffractogram (or powder diagram), obtained from a monocrystal of the zwitterion, as described in Example 1 (part 1.5.2).

In the text hereinbelow, the starting compounds and the reagents mentioned for the process according to the invention, when their mode of preparation is not described, are commercially available or described in the literature, or may be prepared according to methods that are described therein or that are known to those skilled in the art.

A subject of the present invention is thus, most particularly, a novel intermediate compound which, without wishing to be bound by any theory, is in the form of a zwitterion having the formula (I) below (which may thus be referred to as an N-methylnaltrexone zwitterion):

The respective diastereoisomers of (R) and (S) configurations relative to the nitrogen atom of the N-methylnaltrexone zwitterion, and also mixtures thereof, including racemic mixtures, form part of the invention.

Besides its anhydrous form, the N-methylnaltrexone zwitterion may also exist in the form of a hydrate.

According to the invention, the term "hydrate" means a form of association or combination of the compound of formula (I) with one or more molecules of water of crystallization in the crystal lattice, i.e. excluding the water of insertion into the microchannels of the crystals (or "water of impregnation"), the hydrate possibly being determined firstly by analysis on a monocrystal and then confirmed routinely by comparative analysis of diffractograms (or powder diagrams) as is well known to those skilled in the art and illustrated in Example 1.

Such hydrates also form part of the invention. For example, the hemihydrate, dihydrate and trihydrate forms may be mentioned.

According to a particular embodiment of the invention, the zwitterion of formula (I) has an (R) configuration relative to the nitrogen atom and is in dihydrate form. This novel N-methylnaltrexone zwitterion compound, of formula (I), may advantageously be prepared via a process comprising the step that consists in reacting N-methylnaltrexone methyl sulfate in aqueous solution with an alkaline agent chosen from the group constituted by sodium carbonate ($Na_2CO_3$), potassium carbonate, calcium carbonate, magnesium carbonate, cesium carbonate, strontium carbonate and mixtures thereof, at a pH of the aqueous solution of between 7 and 10 and preferably between 9.5 and 9.8 and at a temperature of between 15 and 30° C., preferably about 20° C.

A subject of the present invention is also a process for preparing N-methylnaltrexone bromide, comprising at least the steps consisting in:

(i) reacting N-methylnaltrexone methyl sulfate in aqueous solution with an alkaline agent chosen from the group constituted by sodium carbonate, potassium carbonate, calcium carbonate, magnesium carbonate, cesium carbonate, strontium carbonate and mixtures thereof, at a pH of the aqueous reaction medium of between 7 and 10 and preferably between 9.5 and 9.8 and at a temperature of between 15 and 30° C., preferably about 20° C., and then in (ii) reacting the product thus obtained with hydrobromic acid, preferably of 48% concentration, which is added for a pH of the aqueous reaction medium of between 0.5 and 5 and preferably of about 1, and the reagents are preferably left in contact with stirring for a further one hour, in order thus to obtain the N-methylnaltrexone bromide.

Preferably, the alkaline agent is chosen from the group constituted by sodium carbonate and potassium carbonate, and mixtures thereof.

According to one particular embodiment, methanol may be added at the end of step (ii) described above, the reaction medium is heated to a temperature of between 20 and 80° C., for example between 50 and 70° C., preferably about 60° C., until dissolution is virtually complete, and the remaining light insoluble matter is then separated out by filtration, in order subsequently to cool the methanol/water filtrate, preferably to about 0° C., in order to crystallize therefrom the desired N-methylnaltrexone bromide.

According to another particularly preferred embodiment, the insoluble product obtained at the end of step (i) described above is isolated after filtration by suction, and is then suspended in a methanol/water mixture, preferably of 4/1, thus constituting the aqueous reaction medium for step (ii) in which is performed the reaction with hydrobromic acid, preferably at 48% concentration, which is added, for a pH of the aqueous reaction medium of between 0.5 and 5 and preferably of about 3, at a temperature of between 20 and 80° C., for example between 50 and 70° C., preferably 60° C., until dissolution is almost complete, and the remaining light insoluble matter is then separated out by filtration, in order to subsequently cool the filtrate, preferably to about 0° C., to crystallize therefrom the desired N-methylnaltrexone bromide.

Recrystallization in a methanol/water mixture (of N-methylnaltrexone bromide) or optional washing of the isolated product (N-methylnaltrexone zwitterion) with an organic solvent (for example methanol) makes it possible to remove the lipophilic impurity, O-benzyl-N-methylnaltrexone bromide that may still be present.

The process according to the invention may advantageously include a step of purification of the N-methylnaltrexone bromide thus obtained, by dissolution in an acetone/water mixture, preferably of 80/20, heating to reflux, preferably for at least about 15 minutes, and then separation by hot filtration, precipitation of the N-methylnaltrexone bromide by placing the hot filtrate in contact with warm acetone, preferably of about 50° C., and cooling of the reaction medium to a temperature below 0° C., preferably −2° C., the N-methylnaltrexone bromide thus precipitated being recovered by filtration, and dried.

This step of purification of the N-methylnaltrexone bromide may also be performed via dissolution in a methanol/water mixture or in water alone; similar yields and qualities of the same chemical species are then obtained.

In the process described below, the N-methylnaltrexone methyl sulfate may be advantageously obtained by subjecting O-benzyl-N-methylnaltrexone methyl sulfate to a hydrogenation step.

This hydrogenation step may advantageously be performed as described in Example 1 below, and even more generally by subjecting O-benzyl-N-methylnaltrexone methyl sulfate, in the form of an aqueous solution, to a hydrogenation on 5% palladium-on-charcoal, the reaction medium being maintained at a temperature of between 30 and 50° C., preferably 40° C., under a pressure of about 2.5 bar of hydrogen, for at least about 2 hours for complete O-debenzylation. The reaction medium is then cooled and the catalytic system removed by filtration.

The product obtained may advantageously not be isolated, which makes it possible to avoid any contact with the residual dimethyl sulfate (highly toxic product).

In the process according to the invention, O-benzyl-N-methylnaltrexone methyl sulfate may be advantageously obtained by reacting O-benzylnaltrexone with dimethyl sulfate, in acetone, in the presence of sodium hydrogen carbonate, the reaction medium being refluxed for a sufficient time, preferably at least about 72 hours, for acceptable disappearance of the O-benzylnaltrexone compound, the reaction monitoring possibly being monitored in a known manner, for example by HPLC monitoring. A subject of the present invention is also the novel intermediate compound O-benzyl-N-methylnaltrexone methyl sulfate, thus obtained.

The respective diastereoisomers of (R) and (S) configurations relative to the nitrogen atom of O-benzyl-N-methylnaltrexone methyl sulfate, and also mixtures thereof, including racemic mixtures, form part of the invention.

In particular, the benzyl protecting group on the phenolic oxygen most particularly has a twofold advantage:
  cleavage without introduction and formation of an ionic product: only hydrogen is used, and the toluene formed is readily removed;

hydrogenation makes it possible to reduce the amount of 7,8-didehydro-N-methylnaltrexone (undesirable conjugated ketone) in the final product after hydrogenation of the double bond.

Moreover, the process according to the invention provides excellent diastereoselectivity upstream and for the isolation in N-methylnaltrexone zwitterion form, and for the production of the desired final product, i.e. (R)—N-methylnaltrexone.

In the process according to the invention, the O-benzylnaltrexone may be advantageously obtained by reacting naltrexone hydrochloride, or base naltrexone, with benzyl bromide, in acetone, in the presence of potassium carbonate, the reaction medium being maintained at reflux, preferably at a temperature of about 60° C., for about 2 hours, and then cooled to room temperature (about 20° C.) in order to subsequently filter, and optionally wash with acetone, and the acetone is evaporated from the filtrate to obtain the desired compound in the form of an oil. Preferably, this oil is taken up, for example, in dichloromethane and washed, for example, with dilute (3%) sodium hydroxide.

This liquid extraction in basic medium makes it possible to totally remove the residual non-benzylated naltrexone and to avoid the formation of the impurity 3-O-methyl-N-methylnaltrexone in the alkylation/quaternization step.

The product may advantageously not be isolated, which makes it possible to avoid manipulating a medium containing benzyl bromide, which is a lachrymogenic and toxic product.

Finally, in the process according to the invention, the naltrexone hydrochloride or the base naltrexone may be advantageously obtained by reacting noroxymorphone hydrochloride with bromomethylcyclopropane, in dimethylacetamide, in the presence of sodium hydrogen carbonate, the reaction medium being heated to a temperature of between 60 and 75° C. and preferably between 65 and 69° C., as described, for example, in step 1 of the process of Example 1.

FIG. 1 represents a theoretical diffractogram (or powder diagram), obtained from a monocrystal of the zwitterion, as described in Example 1 (part 1.5.2).

Figure 2:
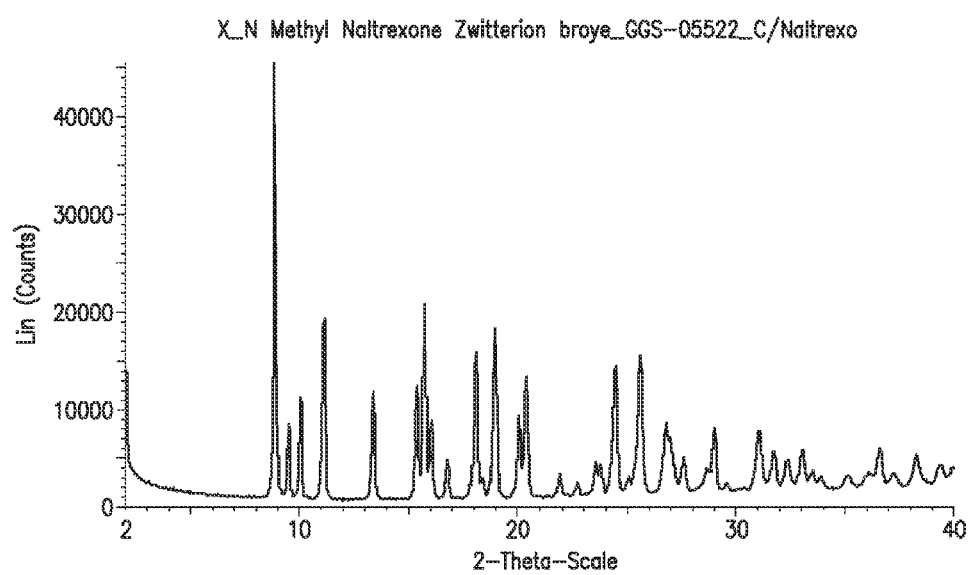
FIG. 2 represents an experimental diffractogram (or powder diagram), obtained from the zwitterion, as described in Example 1 (part 1.5.2).

FIG. 2 represents an experimental diffractogram (or powder diagram), obtained from the zwitterion, as described in Example 1 (part 1.5.2).

The examples that follow are intended to illustrate the present invention, in a non-limiting manner, and should therefore not be interpreted as possibly limiting its scope.

Unless otherwise mentioned, the NMR data below are obtained with TMS (tetramethylsilane) as reference.

EXAMPLE 1

Preparation of N-methylnaltrexone Bromide 1.1 Preparation of Crude Base Naltrexone (Step 1; N-alkylation)

100 g (0.27 mol) of noroxymorphone hydrochloride, 80.8 g (0.96 mol; 3.55 eq.) of sodium hydrogen carbonate and 300 ml of dimethylacetamide are successively introduced into a 500 ml reactor equipped with a condenser and a mechanical stirrer. The reaction medium is heated to between 65° C. and 69° C.

At the end of the observed evolution of gas (about 10 minutes), 35 ml of bromomethylcyclopropane (0.44 mol; 1.6 eq.) are introduced over 30 minutes while keeping the temperature at 69° C.

The N-alkylation is complete in about 6 hours, and the reaction progress is monitored by HPLC analysis (residual content of noroxymorphone less than or equal to 0.5%). The reaction medium is cooled to 50° C. and then poured with stirring over 1 hour into a mixture of 1000 ml of water and 100 g of sodium chloride preheated to 50° C.

The pH is adjusted to 8.6-9 by addition of 8 ml of 30% sodium hydroxide. The product obtained is isolated by filtration at 15° C. and dried in an oven under vacuum at 50° C. for 14 hours.

86 g of crude naltrexone are finally obtained (yield: 88.6%) (HPLC in accordance with the standard and in accordance regarding the $^1$H and $^{13}$C NMR and mass structures).

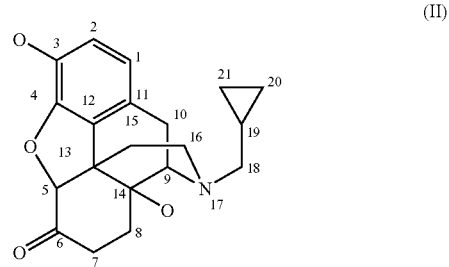

(II)

$^1$H NMR: (ppm; ±0.01 ppm): 0.45 to 0.65 (2H, CH$_2$ (20/21), unresolved complex); 0.41 and 0.66 (2H, CH$_2$ (20/21), two multiplets); 1.11 (1H, CH (19), multiplet); 1.47 and 2.72 (2H, CH$_2$(15), multiplet and dt); 1.50 and 2.05 (2H, CH$_2$ (8), two multiplets); 2.10 and 3.03 (2H, CH$_2$ (7), two multiplets); 2.48 and 3.03 (2H, CH$_2$ (16), two multiplets); 2.97 and 3.32 (2H, CH$_2$(18), two multiplets); 4.02 (1H, CH (9), doublet; J=6.0 Hz) ±0.5 Hz); 5.04 (1H, CH (5), singlet); 6.71 (1H, CH(2), doublet; J=8 Hz); 7.11 (1H, COH (14), singlet); 9.05 (1H, NH, singlet); 9.05 (1H, COH (3), singlet).

$^{13}$C NMR (ppm±0.1 ppm): 2.6 and 5.0 (C20 and C21); 5.6 (C19); 22.8 (C10); 27.1 (C15); 30.6 (C8), 35 (C7); 46 (C16); 48.5 (C13); 56.6 (C18); 60.8 (C9); 69.7 (C14); 88.5 (C5); 118.0 (C2); 119.7 (C1); 120.4 (C11); 127.8 (C12); 140.1 (C4); 143.5 (C6).

Mass (chemical ionization (M+H)$^+$=342.2

1.2 Preparation of O-benzylnaltrexone (Step 2; O-Benzylation)

5.0 g (0.014 mol) of naltrexone hydrochloride (the base may be used), 5.0 g (0.036 mol; 2.58 eq.) of potassium carbonate and 25 ml of acetone are successively added to a 50 ml reactor equipped with a condenser and a mechanical stirrer. 2.6 g (0.015 mol; 1.08 eq.) of benzyl bromide are then added over 10 minutes at 20° C. with stirring. The reaction medium is refluxed (60° C.) for 2 hours and then cooled to 20° C. and filtered. The filter cake is washed with twice 25 ml of acetone.

The acetone is evaporated off under vacuum and the residual oil is taken up in 40 ml of dichloromethane and then washed with 3 times 25 ml of dilute (3%) sodium hydroxide.

This liquid extraction in basic medium makes it possible to totally remove the residual non-benzylated naltrexone and to avoid the formation of the impurity 3-O-methyl-N-methylnaltrexone in the quaternization step 3.

After performing separations of the phases by settling and extractions, the dichloromethane solution is concentrated until no further distillation takes place, and is then used in the following stage without further purification.

The product is not isolated, to avoid manipulating a medium containing benzyl bromide, which is a lachrymogenic and toxic product.

Structural analysis: a sample of the oil obtained is taken to isolate the O-benzylnaltrexone product in hydrochloride form (the O-benzylnaltrexone hydrochloride is obtained by dissolving the base in oil form in MTBE—or methyl tert-butyl ether—and adding 35% hydrochloric acid).

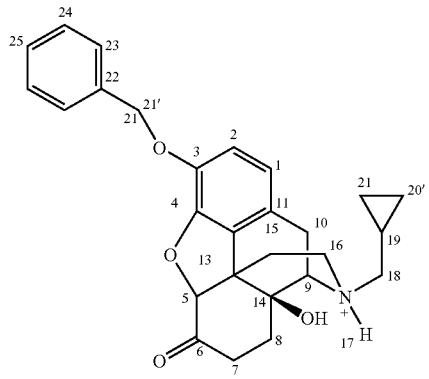

$^1$H NMR (ppm±0.01 ppm): 1.2 (2H,CH$_2$ (20), multiplet J=6 Hz; 0.46 and 1.20 (2H,CH$_2$ (20'), multiplet, J=5 Hz); 1.2 (1H, CH(19), multiplet, J=7.0 Hz); 3.2 (2H,CH$_2$, broad signals); 1.67 and 3.2 (2H, C HZ (15), dd; J=13.8, J=3.0 Hz, broad signals); 1.64 and 2.51 (2H,C Hz (8), td, J=3.2 Hz, broad signals); 2.33 and 3.25 (2H,CH$_2$(7), d, J=14.5 Hz, J=5.0, td J=14.6 Hz, J=2.0 Hz); 2.51 and 3.45 (2H,CH$_2$ (16), broad signal); 2.94 and 3.45 (2H,CH$_2$(18), dd; J=12.5 Hz, J=7.2 Hz, broad signal), 4.51 (1H, CH (9), broad singlet); 5.22 and 5.30 (2H, CH$_2$ (21) and CH2 (21'); J=12.1 Hz); 5.00 (1H, CH (5); broad singlet); 6.79 (1H, CH(2) and CH(1), AB system; J=8.3 Hz); 6.65 (1H, CH (1) and CH(2), AB system, J=8.3 Hz); 6.65 (1H, CH(23)CH(24), benzyl system) 6.65 (1H, CH(25), benzyl system); 6.65 (1H,CH(24),CH(23), benzyl system).

$^{13}$C NMR (ppm±0.1 ppm): 3.8 (C20); (C20'); 6.1 (C19); 24.2 (C10); 27.5 (C15); 31.2 (C8); 35.4 (C7); 47.0 (C16); 49.2 (C13);; 58.4 (C18); 61.2 (C9); 70.4 (C14): 72.1 (C21 and 21'); 89.8 (C5); 118.9 (C2 and C1); 119.9 (C1 and C2); 121.6 (C22); 127.8 (C23 and C24); 128 (C25); 128.5 (C24 and C23); 137 (C3); 142.8 (C11 and C12); 145.9 (C12 and C11); 207.1 (C6).

Mass (ionization MH$^+$)=432.5.

1.3 Preparation of N-methyl-O-benzylnaltrexone Methyl Sulfate (Step 3: N-methylation, Quaternization)

The oil obtained in the preceding stage is dissolved in 20 ml of acetone and then poured at 20° C. with stirring into a dry 50 ml reactor containing 1.3 g (0.015 mol; 1.08 eq.) of sodium hydrogen carbonate; 6.7 g (0.053 mol; 3.53 eq.) of dimethyl sulfate are then added over 10 minutes.

The reaction medium is refluxed with stirring for a minimum of 72 hours until the O-benzylnaltrexone has totally disappeared (HPLC monitoring).

The reaction medium is cooled to 20° C. and then filtered.

The filter cake is washed with twice 10 ml of acetone and then placed in basic solution (NaHCO$_3$ or NaOH). This filtrate is stored at 20° C. for use in the following stage without isolation.

The product is not isolated, to avoid manipulating a product containing dimethyl sulfate. Similarly, the filter cake (NaHCO$_3$+dimethyl sulfate residue) is dissolved on the filter without isolation, with basic medium, so as to destroy the dimethyl sulfate and form sodium methyl sulfate (non-toxic).

Structural analysis: a small amount of the product is taken up and purified by preparative chromatography in order thus to obtain a sample analyzed as follows.

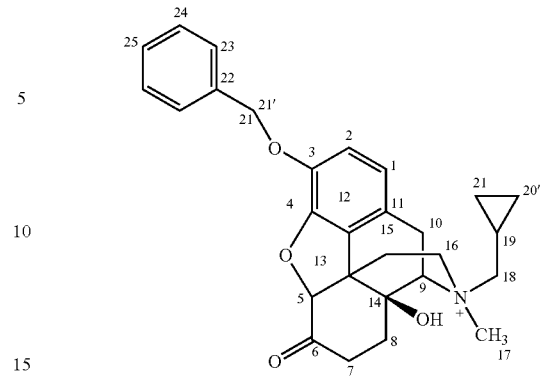

$^1$H NMR (ppm±0.01 ppm); 0.41 and 0.88 (2H, CH$_2$ (20); multiplet, J=5.0 Hz); 1.2 (1H, CH (19), multiplet, J=5.0 Hz); 0.55 and 1.06 (2H CH$_2$ (20'); multiplet, J=5.0 Hz); 1.75 and 3.0 (2H, CH$_2$ (15), d; J=12.5 Hz); 3.1 and 3.41 (2H, CH$_2$ (10), multiplet d, J=5.5 Hz, J=20.1 Hz); 1.63 and 2.43 (2H, CH$_2$ (8), td, doublet of multiplets, J=13.7 Hz, J=3.2 Hz, J=11.5 Hz); 2.25 and 3.16 (2H, CH$_2$(7), dt, unresolved complex, J=14.9 Hz; J=2.8 Hz); 3.66 (3H, CH$_3$ (17), s); 2.9 and 3.15 (2H, CH$_2$(16), multiplet, H=3 Hz); 5.03 (1H,CH(9), d, J=4.1 Hz) 5.20 and 5.28 (2H, CH$_2$ (21) and (21', d, J=12.0 Hz); 2.60 and 3.77 (2H, CH$_2$(18); dd, dd, J=13.5 Hz, J=9.4 Hz; J=13.5 Hz, J=3.6 Hz); 5.05 (1H, CH(5), s); 6.82 (2H,CH(2) and CH(1), AB system, J=8.3 Hz); 6.68 (2H, CH(1) and CH(2), AB system, J=8.3 Hz); 7.33 (2H, CH (23) and CH(24), benzyl system) 7.33 (1H, CH (25), benzyl system; 7.33 (2H CH(23) and CH (24), benzyl system).

$^{13}$C NMR (ppm±0.1 ppm): 3.6 (C20); 4.2 (C19); 7.1 (C20'); 25 (C15); 27.9 (C10); 32.5 (C8); 35.3 (C7); 49.0 (C13); 53.8 (C17); 58 (C16); 71.4 (C9); 72 (C14); 7.21 (C21 and 21'), 73.2 (C18); 89.6 (C5); 119.0 (C2 and C1); 120.3 (C(1) and C(2)); 121.1 (C22); 127.8 (C23 and C24) 128.1 (C25); 128.5 (C24 and C23); 136.8 (C3); 143.3 (C11 and C12); 146.0 (C12 and C11); 206.8 (C6).

Mass (chemical ionization M$^+$)=466.

By HPLC analysis, the existence of the (R) and (S) respective configurations with respect to the nitrogen atom is observed, in an R/S configuration ratio of 96.6/3.4.

1.4 Preparation of N-methylnaltrexone Methyl Sulfate (Step 4: O-debenzylation)

The above acetone solution is concentrated to one third, 100 ml of water are then added and the distillation under vacuum is continued until the acetone has been removed.

After cooling to 20° C., the above solution is added to 5% palladium-on-charcoal (0.3 g).

The reaction medium is then warmed to 40° C. Purging sequences (N$_2$/H$_2$) are performed, followed by establishing a pressure of 2.5 bar of hydrogen.

The O-debenzylation is complete after about 2 hours, with monitoring by HPLC (content of N-methyl-O-benzylnaltrexone methyl sulfate less than 0.5%). The reaction medium is cooled to 20° C. and filtered to remove the catalyst.

The aqueous solution of N-methylnaltrexone methyl sulfate thus obtained is used directly in the following stage.

The benzyl protecting group on the phenolic oxygen has a twofold advantage:
  cleavage without introduction and formation of an ionic product: only hydrogen is used, and the toluene formed is readily removed;
  hydrogenation makes it possible to reduce the amount of 7,8-didehydro-N-methylnaltrexone (conjugated ketone, thus warning structure) in the final product after hydrogenation of the double bond.

The product is not isolated, to avoid contact with the residual dimethyl sulfate (highly toxic product).

1.5 Preparation of N-methylnaltrexone Bromide (Step 5: Methyl Sulfate/Bromide Exchange)

1.5.1 N-methylnaltrexone Zwitterion (Isolation of this Compound)

The aqueous solution from stage 4 is concentrated under vacuum until a residual volume of 30 ml is obtained, and 1 g of $Na_2CO_3$ is then added until a pH of about 9.5 to 9.8 is obtained (natural pH of sodium carbonate in water).

The reaction medium is maintained at 20° C. with stirring for 1 hour.

The use of sodium carbonate in this step makes it possible in particular to destroy the dimethyl sulfate after 1 minute of contact.

The insoluble matter formed is filtered off by suction, and it is thus seen that an N-methylnaltrexone zwitterion may exist under these particular pH conditions (with the use of sodium carbonate $Na_2CO_3$).

Structural analysis: a portion of the suction-filtered insoluble matter obtained above is suspended in water at a pH of about 9.5 (which makes it possible to purify the zwitterion (i.e., the double ion) before analysis by "desalting") and is then isolated by suction filtration and drying.

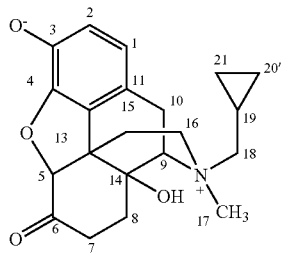

$^1$H NMR (ppm±0.01 ppm); 0.0 and 0.48 (2H, $CH_2$(C20)); multiplet, J=5.0 Hz, J=4.5 Hz); 0.88 (1 h, CH (19), multiplet, J=4.0 Hz); 0.29 and 0.60 (2H, C Hz(20'), multiplet, J=4.8 Hz); 1.49 and 2.51 (2H, $CH_2$ (15), doublet of multiplets, J=10.4 Hz) 2.79 and 3.29 (2H, $CH_2$(10), d, J=19.9 Hz); 1.57 and 1.97 (2H, $CH_2$(8) or (7); dd, doublet of multiplets, J=13.8 Hz, J=3.9 Hz, J=15.2 Hz); 1.77 and 2.71 (2H, $CH_2$ (7) or (8), doublet of multiplets, dt, J=13.9 Hz, J=14.9 Hz, J=5.4 Hz); 3.38 (3H, $CH_3$(17), s); 2.80 and 3.03 (2H, $CH_2$(16); dd; J=13.0 Hz, J=3.5 Hz); 3.72 (1H, CH(9), d, J=4.6 Hz); 2.47 and 3.60 (2H, $CH_2$ (18); t, dd, J=9.8 Hz, J=13.9 Hz, J=3.5 Hz); 4.54 (1H, CH(5), s), 6.35 (2H, CH(2) and CH(1), AB system, J=8.2 Hz); 6.26 (2H, CH(1) and CH(2), AB system, J=8.1 Hz).

$^{13}$C NMR (ppm±0.1 ppm)=0.0 (C20); 1.3 (C19); 3.7 (C20'); 22.2 (C15); 25.4 (C10); 30.2 (C8 or C7); 30.3 (C7 or C8); 47.0 (C13); 51.0 (C17); 55.5 (C16); 69.8 (C9); 70.3 (C18); 70.5 (C14); 111.9 (C5); 118.9 (C2 and C1); 119.6 (C1 and C2): 124.1 (C3); 143.8 (C11 and C12); 147.8 (C12 and C11); 211.5 (C6).

Mass (chemical ionization MH$^+$)=356.

Elemental Analysis:
theoretical calculated values (C 60.7%; H 7.68%; N 3.37%; O 28.24%).
experimental values (C 61.64%; H 7.6%; N 3.19%).

These two values take into account a water content of 14.45%, which may be interpreted in principle as a degree of hydration of a trihydrate form (3H$_2$O). However, the following analyses were also performed.

Analysis by Powder X-Ray Diffraction (XRD):

The analysis is performed in a D5005 diffractometer from the company Brüker. The angular range is between 2.00 and 40.00°2θ in increments of 0.02°2θ and 2 seconds per increment. The generator is set at 50 kV-40 mA for a copper tube whose incident beam wavelength is 1.54056 Å.

The double ion purified by "desalting" as described above gives an experimental diffractogram (see FIG. 2) that proves to be identical by comparison with a theoretical diffractogram corresponding to a dihydrate (2H$_2$O) crystal structure. This theoretical diffractogram is obtained by simulation (see FIG. 1; Mercury® software) from the results of a crystal study on a monocrystal of the same zwitterion purified by "desalting".

The difference in degree of hydration obtained on a monocrystal (2H$_2$O) and on the elemental analysis (3H$_2$O) is explained by the presence of two molecules of water of crystallization in the structure of the crystal lattice and of one water molecule originating from the water of insertion into the microchannels of the crystals (water of impregnation).

By HPLC analysis, the existence of the (R) and (S) respective configurations with respect to the nitrogen atom is observed, in an R/S configuration ratio of 98/2.

1.5.2 N-methylnaltrexone Bromide

The preceding insoluble matter is suspended in 20 ml of an MeOH/water mixture (4/1), hydrobromic acid is added (qs pH=3) and the reaction medium is then maintained at 60° C. until the dissolution is virtually complete.

The light insoluble matter (undissolved N-methylnaltrexone) is filtered off and the filtrate is then cooled to 0° C. The crude N-methylnaltrexone bromide crystallizes on cooling, and is then filtered off by suction.

Recrystallization from a methanol/water mixture (of the N-methylnaltrexone bromide) or optional washing of the isolated product ("zwitterion") with an organic solvent (for example methanol) allows the lipophilic impurity O-benzyl-N-methylnaltrexone bromide to be removed.

1.6 Preparation of Pure N-methylnaltrexone Bromide (Step 6: Recrystallization from Acetone/Water)

5.6 g of crude N-methylnaltrexone bromide (dry), 7.5 ml of water and 22 ml of acetone (i.e. 5 volumes of an 80/20 acetone/water mixture) are successively introduced into a 50 ml reactor equipped with a condenser. The medium is refluxed for 15 minutes. The cloudy material (undissolved N-methylnaltrexone bromide) is filtered off while hot (60° C.) and the hot filtrate is poured into 10 ml of acetone at 50° C.

The product precipitates in solution, the solution is cooled to −2° C. and the precipitate is filtered off.

The product is dried under vacuum at 20° C. for 48 hours.

4.3 g of pure N-methylnaltrexone bromide are finally obtained (76% yield relative to the crude N-methylnaltrexone bromide, and 70% yield relative to the starting naltrexone hydrochloride).

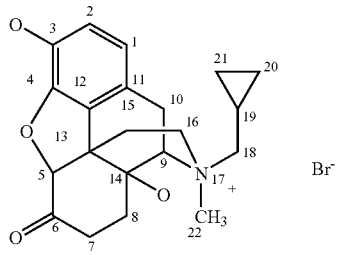

(III)

Physical Characteristics:
Melting point: (DSC): 262° C.
$^1$H NMR (ppm, ±0.01): identical to Naltrexone except for: 3.7 (3H, C(22) singlet); $^{13}$C (ppm±0.01) identical to Naltrexone except for: 58 (C(22)).
Mass: (chemical ionization): (M+H)=356.3.
Complies in all respects with the literature data.

EXAMPLE 2

Preparation of N-methylnaltrexone Bromide (Step 5: Methyl Sulfate/Bromide Exchange, Variant without Isolation of the Intermediate The aqueous solution from step 4 of Example 1 is concentrated under vacuum until a residual volume of 30 ml is obtained, and 1 g of $Na_2CO_3$ is then introduced until a pH of about 9.5 to 9.8 is obtained (natural pH of sodium carbonate in water).

The reaction medium is maintained at 20° C. with stirring for 1 hour, 2.1 ml of 48% hydrobromic acid are then added over 1 hour, i.e. down to a pH of about 1, and the reagents are left in contact with stirring for a further 1 hour.

The insoluble matter of the reaction medium is filtered off by suction and this filter cake is washed with 10 ml of acetone and then dried in an oven under vacuum (10 mmHg) at 40° C. for 12 hours.

9.35 g of a mixture of crude N-methylnaltrexone bromide and of mineral salts (NaBr and $NaMeSO_4$; titer of crude N-methylnaltrexone bromide: 50%) are obtained.

EXAMPLE 3

Preparation of N-methylnaltrexone Bromide (Step 5: Methyl Sulfate/Bromide Exchange, Variant without Isolation of the Intermediate, with MeOH)

In step 5 of the process of Example 1, after treatment with HBr, 40 ml of methanol are added and the mixture is then maintained at 60° C. until the dissolution is virtually complete. The light insoluble matter (undissolved N-methylnaltrexone bromide) is filtered off.

The filtrate (MeOH/$H_2O$ mixture) is cooled to 0° C. The crude MNTX bromide crystallizes on cooling, and is then filtered off by suction.

The major advantage of this variant is the solubilization of mineral salts (NaBr, $NaCH_3SO_4$) in the methanol/water mixture, whereas NaBr is slightly soluble in the ethanol/water mixture.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. N-Methylnaltrexone zwitterion, of formula (I), substantially in the anhydrous form or a hydrate thereof:

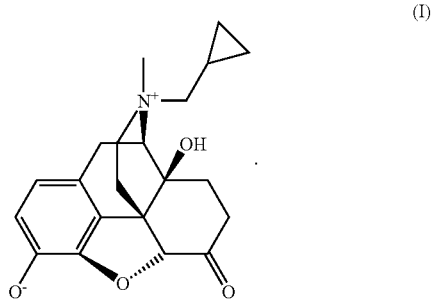

(I)

2. N-methylnaltrexone zwitterion according to claim 1, which is in the (R) configuration relative to the nitrogen atom.

3. N-methylnaltrexone zwitterion according to claim 1, which is in the (S) configuration relative to the nitrogen atom.

4. N-methylnaltrexone zwitterion according to claim 1, which is in the form of a hydrate chosen from hemihydrate, dihydrate or trihydrate.

5. N-methylnaltrexone zwitterion according to claim 2, which is in the form of a hydrate chosen from hemihydrate, dihydrate or trihydrate.

6. N-methylnaltrexone zwitterion according to claim 3, which is in the form of a hydrate chosen from hemihydrate, dihydrate or trihydrate.

7. (R)—N-methylnaltrexone zwitterion, dihydrate.

8. O-Benzyl-N-methylnaltrexone methyl sulfate.

9. O-Benzyl-N-methylnaltrexone methyl sulfate according to claim 8 in the (R) configuration relative to the nitrogen atom.

10. O-Benzyl-N-methylnaltrexone methyl sulfate according to claim 8 in the (S) configuration relative to the nitrogen atom.

* * * * *